US00PP20355P2

(12) United States Plant Patent
Pieters

(10) Patent No.: US PP20,355 P2
(45) Date of Patent: Sep. 22, 2009

(54) *CHRYSANTHEMUM* PLANT NAMED 'PPP COL OR07'

(50) Latin Name: *Chrysanthemum morifolium*
Varietal Denomination: PPP COL OR07

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/218,798

(22) Filed: Jul. 18, 2008

(51) Int. Cl.
*A01H 5/00* (2006.01)

(52) U.S. Cl. ..... Plt./290

(58) Field of Classification Search ..... Plt./290, Plt./287, 296
See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by small decorative type inflorescences, consistent flowering response to short days, blooming consistently after 49 days of short day length, bronze inflorescences with a darker red center, free branching habit, and a consistent natural season flowering habit during the second week of September.

1 Drawing Sheet

Latin name of the genus and species: *Chrysanthemum morifolium.*

Variety denomination: 'PPP COL OR07'.

BACKGROUND OF THE INVENTION

The new cultivar 'PPP COL OR07' is a product of a cross between the male parent 'Forza Orange' and the female parent 'Medonia Red' (neither are under patent in the United States). The new cultivar was discovered and selected by Dirk Pieters in September of 2001 in Oostnieuwkerke, Belgium.

Asexual reproduction of the new cultivar 'PPP COL OR07' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP COL OR07' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP COL OR07.' These characteristics in combination distinguish 'PPP COL OR07' as a new and distinct *Chrysanthemum* cultivar:

1. Small, bronze decorative-type inflorescences with a darker red center;
2. Consistent natural season flowering habit during the second week of September;
3. Free branching habit; and
4. Consistent flowering response to short days, blooming consistently after 49 days of short day length.

Plants of the new cultivar 'PPP COL OR07' are similar to plants of the male parent variety, 'Forza Orange' in most horticultural characteristics, however plants of the new cultivar 'PPP COL OR07' are taller and wider. Also, the male parent 'Forza Orange' has more inflorescences per lateral branch. Additionally, 'PPP COL OR07' has a smaller inflorescence diameter and the ray florets are more orange than the ray florets of the male parent. Finally, 'PPP COL OR07' blooms three to four weeks earlier than the male parent 'Forza Orange.'

Plants of the new cultivar 'PPP COL OR07' are similar to plants of the female parent variety, 'Medonia Red' in most horticultural characteristics, however plants of the new cultivar 'PPP COL OR07' are shorter. Also, the new cultivar 'PPP COL OR07' has a bigger inflorescence diameter. Additionally, 'PPP COL OR07' has more yellow-orange ray florets compared to the red ray florets of the female parent. Finally, 'PPP COL OR07' naturally blooms a month earlier than 'Medonia Red.'

In comparison to the commercially available variety 'PPP CON OR05' (U.S. Plant Pat. No. 18,094), 'PPP COL OR07' is smaller in both height and plant spread. Additionally, the new variety 'PPP COL OR07' has a smaller inflorescence. Further, the inflorescences of the new variety 'PPP COL OR07' are greyed-orange with a dark red center compared to the bright orange inflorescences of the comparable variety.

BRIEF DESCRIPTION OF THE PHOTOGRAPH

The accompanying photograph illustrates in full color a typical plant of 'PPP COL OR07' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP COL OR07' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP COL OR07.'
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 16 cm.
Plant spread: Approximately 30 cm.
Growth rate: Moderate.
Branching characteristics: Free Branching.
Length of lateral branches: Approximately 11 cm.
Number of leaves per lateral branch: Approximately 25.
Age of plant described: Approximately 140 days.

FOLIAGE

Leaf:
*Arrangement.*—Alternate single.
*Average length.*—Approximately 3 cm.
*Average width.*—Approximately 1.2 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 0.9 cm.
*Color.*—Young foliage upper side: Near Yellow-Green 147A. Young foliage under side: Near Yellow-Green 147B. Mature foliage upper side: Near Yellow-Green 147A. Mature foliage under side: Near Yellow-Green 147B.
*Venation.*—Type: Palmately net. Venation color upper side: Near Green 138B. Venation color under side: Near Green 138C.
Petiole:
*Average length.*—Approximately 0.7 cm.
*Color.*—Near Green 138B.
*Diameter.*—Approximately 0.1 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the second week in September.
*Number of inflorescences per lateral branch.*—Approximately 6.
*Inflorescence diameter.*—Approximately 3.8 cm.
*Inflorescence depth.*—Approximately 1.4 cm.
*Inflorescence longevity on plant.*—Approximately 28 to 31 days.
*Persistence.*—Persistent.
Ray florets:
*Appearance.*—Matte.
*Texture.*—Smooth.
*Average number of ray florets per inflorescence.*—210.
*Shape.*—Oblanceolate.
*Aspect.*—Flat.
*Margin.*—Entire.
*Apex.*—Obtuse.
*Length.*—Approximately 1.3 cm.
*Width.*—Approximately 0.4 cm.
*Color.*—Upper surface at first opening: Near Greyed-Purple 185A. Upper surface at maturity: Near Greyed-Orange 167A with shades of near Yellow 9A rising up in longitudinal lines from the base. Upper surface at fading: Near Greyed-Orange 167B with shades of near Yellow 9A rising up in longitudinal lines from the base. Under surface at first opening: Near Greyed-Purple 185A. Under surface at maturity: Near Greyed-Red 171A with shades of near Yellow 9A rising up in longitudinal lines from the base. Under surface at fading: Near Greyed-Orange 167C with shades of near Yellow 9A rising up in longitudinal lines from the base. Center ray florets: Near Greyed-Red 181A throughout maturity and fading.
Disc florets:
*Appearance.*—Shiny.
*Texture.*—Smooth.
*Average number of florets per disc.*—Approximately 8.
*Shape.*—Cylindric.
*Apex.*—Obtuse.
*Average length.*—Approximately 0.3 cm.
*Average width.*—Approximately 0.1 cm.
*Color.*—At first opening: Near Yellow-Green 154C. At maturity: Near Yellow 13A. At fading: Near Yellow 13A.
Peduncle:
*Length.*—At terminal end (shortest): Approximately 3 cm. At lateral end (longest): Approximately 9.2 cm.
*Angle to stem.*—Acute.
*Strength.*—Moderate.
*Color.*—Near Green 138B.
*Habit.*—Upright.
*Diameter.*—Approximately 0.1 cm.
*Surface texture.*—Lightly pubescent.
Inflorescence bud:
*Length.*—Approximately 0.6 cm.
*Diameter.*—Approximately 1 cm.
*Form.*—Globular.
*Color.*—Near Greyed-Purple 185A.
Involucral bracts (phyllaries):
*Appearance.*—Matte.
*Texture.*—Lightly pubescent.
*Number.*—Approximately 28.
*Shape.*—Ovate.
*Margin.*—Entire.
*Apex.*—Acute.
*Length.*—Approximately 0.5 cm.
*Width.*—Approximately 0.2 cm.
*Color.*—Upper side: Near Green 137A. Under side: Near Green 137B.

REPRODUCTIVE ORGANS

Ray florets:
*Number of pistils per floret.*—1.
*Stigma shape.*—2 branched.
*Stigma color.*—Near Yellow 9A.
*Style color.*—Near Green-Yellow 1D.

*Style length.*—Approximately 0.3 cm.
*Stamens.*—Absent.

Disc florets:
*Number of pistils per floret.*—1.
*Stigma shape.*—Cylindric.
*Stigma color.*—Near Yellow 13A.
*Style length.*—Approximately 0.2 cm.
*Style color.*—Near Green-Yellow 1D.
*Number of stamens per floret.*—Approximately 5.
*Anther shape.*—Tubular.
*Anther color.*—Near Yellow 13A.
*Pollen color.*—Near Yellow 13A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP COL OR07' as herein illustrated and described.

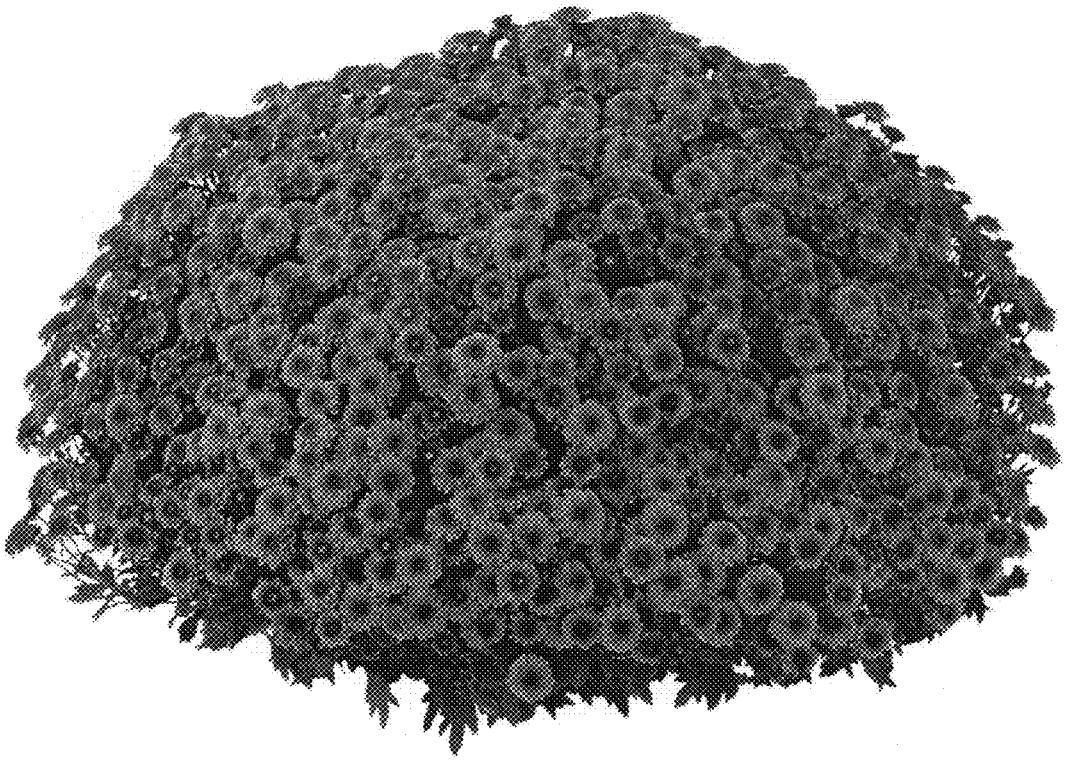

* * * * *